(12) United States Patent
Tsai et al.

(10) Patent No.: US 6,172,191 B1
(45) Date of Patent: Jan. 9, 2001

(54) PROTEIN FOR INHIBITION AND ACTIVATION OF PROTOONCOGENE RAS AND METHOD FOR ISOLATION THEREOF

(76) Inventors: David Tsai; Jenny Yu, both of 2500 Townsgate Rd. Unit C, Westlake Village, CA (US) 91361

( * ) Notice: Under 35 U.S.C. 154(b), the term of this patent shall be extended for 0 days.

(21) Appl. No.: 09/066,238

(22) Filed: Apr. 24, 1998

(51) Int. Cl.[7] .......................... A61K 35/30; C07K 14/47; C12N 5/06

(52) U.S. Cl. ...................... 530/350; 424/174.1; 435/325; 435/7.1; 435/69.1; 435/70.1; 435/71.1; 514/44; 530/388.8; 530/389.7; 530/828; 536/23.5

(58) Field of Search .......................... 424/174.1; 435/325, 435/7.1, 69.1, 70.1, 71.1; 514/44; 530/350, 388.8, 389.7, 828; 536/23.5

(56) References Cited

PUBLICATIONS

Floer et al. The Journal of Biological Chemistry vol. 271, No. 10, Mar. 8, 1996, p. 5313–5316.*
Moore et al. PNAS, USA, vol. 91, Oct. 1994, p 10212–10216 No. 21.*
Bombik, et al. c–AMP and the Cell Cycle: Inhibition of Growth Stimulation; Exptl. Cell Res. 80 (1973), pp. 88–94.
Willingham, et al. Control of DNA Synthesis and Mitosis in 3T3 Cells by Cyclic AMP, Biocmem. and Bio Phy. Research Communications, vol. 48, No. 4 (1972) pp. 743–748.
Boynton, et al. An Examination of the Roles of Cyclic Nucleotides in the Initiation of Cell Proliferation, Life Sciences, vol. 22 (1978) pp. 703–710.
Froelich, et al. "Inhibition of Cell Crowth in the G1 Phase by Adenosine 3', 5'–Cyclic Monophosphate," J. of Cell Bio., vol. 60 (1974) pp. 249–257.
Rechler, et al. "Modulation of Serum–Stimulated DNA Systems in Cutured Human Fibroblasts of cAMP," Exp. Cell Res. 104 (1977) pp. 411–422.
Froelich, et al. :Effect of Adenosine 3'–5'–Cyclic Monophosphate on Cell Proliferation, J. of Cell Bio., vol. 55 (1972) pp. 19–31.
Otten, et al. Regulatin of Cell Growth by Cyclic Adenosine 3',5'–Monophosphate, J. of Biological Chemistry, vol. 247, No. 21 (1972) pp. 7082–7087.
Burger, et al. Growth Control and Cyclic Alterations of Cyclic AMP in the Cell Cycle, Nature New Biology, vol. 239 (1972) pp. 161–163.

* cited by examiner

*Primary Examiner*—Phuong T. Bui
(74) *Attorney, Agent, or Firm*—Trojan Law Offices

(57) ABSTRACT

The method to isolate a protein, designated as p10, which strongly inhibits the activity of H-Ras bound to GTP in vitro while in the presence of cAMP, which inactivates the biological function of Ras is provided. Protein p10 also inhibits intrinsic GTPase activity of Ras without affecting GTP binding activity in vitro, which keeps Ras in its active form and activates Ras biologically. The invention activates or inhibits Ras in a cAMP dependent manner leading to the stimulation or inhibition of cell proliferation.

1 Claim, 7 Drawing Sheets

1. Heated Ras Resin
2. Ras-GDP Resin
3. Ras-GTP Resin

PROTEIN FOR INHIBITION AND ACTIVATION OF PROTOONCOGENE RAS AND METHOD FOR ISOLATION THEREOF

BACKGROUND OF THE INVENTION

Protooncogene Ras has become a central focus in many studies of neoplasia for a variety of reasons. Among these are the finding that Ras plays an important role in regulating cell proliferation (Berridge, M. J. et al. Biochem. J. 230: 345. 1984) and the frequency of the Ras mutations in many tumors; about 50% of human colon carcinomas and 90% of pancreatic carcinomas produce mutant Ras protein. (Varmus, H. E. Ann. Rev. Genet. 18: 553.1984. Farr, C. L. et al. Proc. Natl. Acad. Sci. 85: 1629. 1988. Barbacid, M. Ann. Rev. Biochem. 56: 779. 1997). This data has led to the widely-held belief that Ras proteins play a critical role in the control of carcinogenesis and inhibition of Ras may lead to the inhibition of cancer cell growth. Accordingly, much interest has been directed toward the study of Ras biochemistry, Ras mutation and any protein which might influence the biological activity of Ras.

Ras functions as a signal transducer for cell proliferation. Located on the inner surface of cell membrane, Ras is able to delay proliferative signal from growth factor receptors to the nucleus for initiation of cell growth. Mutations which cause hyperactivity of Ras may lead to cell transformation, which has been shown to occur in many human tumors. (Barbacid, M. Ann. Rev. Biochem. 56: 779.1987).

As with other guanine nucleotide-binding proteins, Ras is thought to be biologically active when bound to GTP. Its intrinsic GTPase converts Ras GTP to Ras GDP, which is thought to be biologically inactive. In our study, we have isolated a protein designated as p10 which, in the presence of cAMP, strongly inhibited H-Ras bound to GTP in vitro, an activity which inactivates the biological function of Ras. Whereas, in the absence of cAMP, p10 inhibited the intrinsic GTPase activity of Ras without affecting its GTP binding activity in vitro, which keeps Ras at its active form and activates Ras biologically. These results show that p10 activates or inhibits Ras in a cAMP dependent manner leading to the stimulation or inhibition of cell proliferation. It is well known that cyclic Adenosine monophosphate (cAMP) plays a critical role in determining if the cell will stay in the G0 phase or progress to the G1 phase [Boyntor, H. L. et al., Adv. Cyclic Nucleo. Res. 15: 193 (1983). Bannai, S. and Sheppard, J. R., Nature 250: 62 (1974). Bombik, B. M. and Burger, M., Exp. Cell Res. 80: 88 (1973). Boynton, A. L. and Whitfield, J. F., J. Cell Physiol. 101: 139 (1979). Boynton, A. L. et al., Life Sci. 22: 703 (1978). Burger, M. M. et al., Nature New Biol. 239: 161 (1972). Otten, J. et al., Biochem. Biophys. Res. Commun. 44: 1192 (1971). Otten, J. et al., J. Biol. Chem. 247: 7082 (1972). Rechler, M. M. et al., Exp. Cell Res. 104: 411 (1977). Rochette-Egly, C. et al., J. Cyclic Nucleotide Res. 5:385 (1979). Sheppard, J. R., Nature New Biol. 236: 14 (1972). L'Allemain, G. et al., Oncogene 14: 1981 (1997). Southgate, K. et al., Atherosclerosis 82: 113 (1990). Tominson, P. R. et al., Biochem Phamacol. 49: 1809 (1995). Indolfi, C. et al., Nat. Med. 3:775 (1997). Kram, R. et al., Proc. Natl. Acad. .Sci. U.S.A. 270: 1432 (1973). Willingham, M. C. et al., Biochem. Biolphys. Res. Commun. 48: 743 (1972). Hogan, B. et al., Cell 2: 229 (1974). Pardee, A. B., Proc.Natl. Acad. Sci. U.S.A. 71: 1286 (1974). Lehnert, S., Exp. Cell Res. 121: 383 (1979). Rozengurt, E. and Pardee, A. B., J. Cell Physiol. 80: 273 (1972). Paul, D. and Walter, S., J. Cell Physiol. 85: 113 (1975). Froehlich, J. E. and Rachmeler, M., J. Cell. Biol. 55: 19 (1972). Froehlich, J. E. and Rachmeler, M., J. Cell. Biol. 60: 249 (1974). Lingwood, C. A. and Thomas, D. B., J. Natl. Cancer Res. 52: 1659 (1974). Frank, W., Exp. Cell Res. 71: 238 (1972). Cho. B. K. and Rose, N. R., Exp. Cell Res. 83: 261 (1974)]. The elevated cAMP level caused by serum starvation is necessary to keep the cell in the quiescent state (G0 state); whereas serum stimulation of the quiescent cell causes the decrease of intracellular cAMP levels which is a signal for the G0 to G1 transition leading to the resumption of cell cycle. On the other hand, protoncogene Ras was found to be a key molecule controlling the cell to leave G0 state (Peeper, D. S. et al., Nature 386: 177 (1997). Dobrowolski, S. et al., Mol. Cell Biol. 14: 5441 (1994)). In the present studies, we found that in the presence of cAMP, p10 functionally inhibits Ras, whereas, in the absence of cAMP, p10 functionally activates Ras. In response to serum starvation, the elevated cAMP levels render p10 to inhibit Ras (by inhibiting Ras GTP binding) causing the cell to enter a quiescent or G0 state. Serum stimulation of a quiescent cell, on the other hand, causes the decrease of intracellular cAMP levels which render p10 to activate Ras (by inhibiting Ras GTPase activity) leading to the G0 to G1 transition and resumption of the cell cycle.

This invention describes the methods for isolation of p10 protein which activates/inhibits Ras in a cAMP dependent manner as well as the biochemical activity of p10 found in our laboratory at Ambryx.

DETAILED DESCRIPTION OF THE INVENTION

This patent application describes the isolation of a protein designated as p10 which can alter the biochemical activity of protooncogene Ras.

(1) Source of p10

P10 was first isolated from bovine brain cell lysate by incubating 5 ml of cAMP conjugated agarose beads (Sigma) with 40 ml of bovine brain cell lysate (5 mg protein/ml) for 18 hr. The cerebra from a bovine was homogenized in ice-cold hypotonic buffer (10 nM Tris-HCl, pH 7.5, 5 mM $MgCl_2$, 1 mM dithiothreitol, 1 mM phenylmethylsulfonyl fluoride). The homogenate was centrifuged at 3000 g for 10 min to remove the unbroken cells. The resulting supernatant was then centrifuged at 100,000 g for 30 min. to obtain a clarified supernatant fraction. The clarified bovine brain cell lysate was used as the source of p10.

(2) Isolation and purification of p10 from bovine cell lysate

Step 1: CAMP agarose beads affinity chromatography p10 was first isolated from bovine brain cell lysate by incubating 5 ml of cAMP conjugated agarose beads (Sigma) with 40 ml of bovine brain cell lysate (5 mg protein/ml) for 18 hr. The cAMP agarose beads were washed 5 times with 200 ml of Tris-HCl buffer (pH 7.5) and the protein that binds cAMP was then eluted with a 10 mM cAMP solution.

Step 2: YM 10 xmembrane separation

The cAMP eluate was separated into a high molecular weight fraction and a low molecular weight fraction by passing the cAMP eluant through a YM 10 membrane (molecular weight cut off=10 Kd). The low molecular weight fraction which passed through YM 10 membrane was collected and used as the source of p10.

Step 3: Heat treatment

The low molecular weight fraction of cAMP eluant prepared in Step 2 was incubated in 100 degree boiling water for 3 minutes. Precipitation was removed by centrifugation at 3,000 g for 10 minutes. p10 was found to remain in supernatant.

Step 4: Q2 anion exchange chromatography

The p10 isolated by previous steps was concentrated and loaded onto a Q2 column (Bio-Rad) which is further developed by a linear gradient constructed by buffer A (10 mM Tris-HCl, pH 7.4) and buffer B (10 mM Tris-HCl, pH 7.4. 0.5 M NaCl) using Bio-Rad's BioLogic HPLC system. The linear gradient was constructed by increasing buffer B from 0% 100% in buffer A within 10 min (20 miniliter elution volume) and thereafter the column was eluted with 100% buffer B for 5 min. p10 was found to be eluted by 0.1–0.15 M NaCl.

As shown in FIG. 1, the purified p10 showed a single protein band with molecular weight of 10 K daltons on SDS-PAGE, suggesting the p10 has been purified to homogeneity.

(3) Biochemical activity of p10

(a) p10 binds (interacts) with protooncogene Ras

We observed that the low molecular weight fraction of the cAMP eluant contained a protein (p10) that was able to bind physically to Ras-GTP and Ras-GDP. In this experiment, bacterially synthesized H-Ras was conjugated to AH-Sepharose 4B by carbodiimide (Pharmacia). Fifty ml of cAMP eluant (low molecular weight fraction) was then incubated with immobilized Ras resin in the presence of 0.5 mg of bovine serum albumin overnight at 4 degrees. After washing extensively with a buffer to remove the unbound materials, the Ras resin was eluted with 10% SDS and the eluted proteins were analyzed by SDS-PAGE on a 20% gel with silver staining. As shown in FIG. 2, we found that a protein with a molecular weight of 10 Kd bound to Ras-GTP and Ras-GDP resins, but not to the heat-denatured Ras conjugated resin. When soluble Ras-GTP was included in the column to compete with the binding of cAMP eluant to immobilized Ras-GTP, the binding of 10 Kd protein to Ras-GTP and Ras-GDP was diminished, suggesting that the binding is specific. The ability of this 10 Kd protein to bind both cAMP and Ras conjugated resins suggests that this protein is a Ras-interacting, cAMP-binding protein. This protein is tentatively designated as p10.

(b) p10 inhibited nucleotides binding activity of Ras in the presence of cAMP

Excited by the finding that p10 physically interacts with Ras, we further tested whether the interaction results in any alteration of the biochemical activities of Ras. Interestingly, we found that the p10 fraction contained an activity to inhibit the nucleotide binding activity of Ras. In this experiment, bacterially synthesized H-Ras was simultaneously incubated with alpha-p32 labelled GTP and the p10 fraction (containing 0.1 mM cAMp) for 20 min at 30° c. The Ras protein was then isolated by a nitrocellulose filter. The p32 GTP retained by nitrocellulose which accounts for the amounts of GTP bound to Ras was then counted by a liquid scintillation counter. As shown in FIG. 3, the p10 fraction strongly inhibited the GTP binding activity of Ras in a dose dependent manner. A similar result was also obtained when GDP instead of GTP was used in this experiment, suggesting that p10 inhibits the GTP/GDP binding activity of H-Ras. In this experiment, cAMP (0.1 mM) was included in the reaction mixture. cAMP alone (up to 1 mM) is ineffective in affecting the GTP binding activity of Ras. Furthermore, preincubation of the p10 fraction with proteinase K eliminated the inhibitory effect of p10, suggesting that a protein is responsible for the inhibition of Ras GTP binding activity.

P10 was first isolated by cAMP affinity chromatography, which suggests that p10 is a cAMP-binding protein. As shown in FIG. 3, in the presence of 0.1 mM cAMP, p10 inhibited Ras GTP binding activity in a dose dependent manner. We have tried to answer a very interesting question: Is cAMP necessary for p10 to inhibit Ras GTP binding activity? Since p10 was isolated by eluting a cAMP affinity column with 10 mM cAMP, the p10 that we isolated should have already been loaded with cAMP. Obviously, to answer the above question, we need to remove bound cAMP from the p10 molecule. Fortunately, we found that bound cAMP can be removed by extensive dialysis of p10. As shown in FIG. 4, when the highly purified p10 (2 ml) was dialyzed against 2 litters of buffer for 2 days, in the absence of added cAMP the GTP binding activity of H-Ras was slightly inhibited (0–10%). However, in the presence of 0.1 mM cAMP, the inhibition of GTP binding activity was largely restored (30–80% inhibition). The cAMP-dependence of p10 in inhibiting Ras GTP binding activity was further demonstrated in FIG. 5. In the absence of exogenous cAMP, the dialyzed purified p10 only slightly (10%) inhibited Ras GTP binding activity. However, the inhibitory activity was boosted several fold by adding exogenous cAMP in a dose dependent manner. Note that as shown in FIG. 5, cAMP alone is not effective in affecting Ras GTP binding activity in all the concentrations we tested.

We have carefully ruled out the possibility that the above observation arose from the artifact caused by the assay we used, or there is a different interpretation on the observation that p10 lowered Ras GTP binding. First, although the above observation was obtained by filter binding assay, we did obtain similar results using immunoprecipitation assay (as described below). Therefore, the results are not due to the choice of a specific assay. Secondly, using a filter binding assay and equilibrium dialysis analysis, we concluded that p10 does not bind GTP, hence, the possibility that p10 competes with Ras for GTP can be ruled out. Third, we were unable to find that the purified p10 contained any protease activity, therefore, it is highly unlikely that the inhibition of GTP binding was due to the cleavage of Ras by p10.

(c) p10 inhibited nucleotides hydrolysis activity of Ras in the absence of cAMP

The above results suggest that p10 inhibited Ras GTP binding activity in a cAMP dependent manner. In the absence of cAMP, p10 was ineffective in inhibiting Ras GTP binding activity. Interestingly, in an attempt to examine the effect of p10 on Ras in the absence of cAMP, we observed that p10, albeit is ineffective in Ras GTP binding activity without cAMP, it inhibited Ras GTPase activity (GTP hydrolysis) in the absence of cAMP. As shown in FIG. 6, p10 was incubated with H-Ras and alpha p-32 GTP in the absence of cAMP, for 20 minutes at 30 degrees. Ras was then immunoprecipitated by anti-Ras antibody Y13-259 and the nucleotides (GTP and GDP) bound to Ras were resolved by a thin layer chromatography and quantified by liquid scintillation counting. We found that, albeit the total number of nucleotides bound to Ras was not significantly altered by p10, the ratio of the number of GTP molecules to the total number of nucleotides that bound to Ras was increased by p10. This result suggests that in the absence of cAMP, p10 inhibited Ras GTPase activity. This notion is further demonstrated in FIG. 7 which shows that p10 inhibited Ras GTPase activity in the absence of cAMP in a dose dependent manner. In the presence of cAMP, p10 decreased the total number of nucleotides bound to Ras without affecting the ratio of GTP to GDP that remained bound to Ras.

(4) Conclusion

This patent application describes purification of a protein with molecular weight of 10 K dalton (designated as p10) that is able to interact with protooncogene Ras. The interaction of p10 with Ras results in the alteration of the biochemical activity of Ras. In the presence of cAMP, p10 inhibited Ras nucleotide binding activity without having effect in Ras GTP hydrolysis activity. Whereas in the absence of cAMP, p10 inhibited Ras GTP hydrolysis activity without having effect in ras GTP binding activity.

As with other guanine nucleotide-binding proteins, Ras is thought to be biologically active when bound to GTP. Its intrinsic GTPase converts Ras-GTP to Ras-GDP, which is thought to be biologically inactive. Accordingly, p10 is able to inhibit Ras function leading to the inhibition of cell proliferation in the presence of cAMP. In the absence of cAMP, however, p10 activates Ras resulting in the stimulation of cell proliferation.

p10 is a Ras-interacting protein that is distinctive from the known Ras-interacting protein such as: Raf (Wittinghofer, A. et al., FEBS LETT. 410: 63 (1997)), GAP (Koyama, S. et al., FEBS LETT. 368: 321 (1995)) and BCL-2 (Chen, C.Y. et al., J. Biol. Chem. 271: 2376 (1996)) in its molecular size and its biochemical activity.

BRIEF DESCRIPTION OF THE FIGURES

FIG. 1. SDS-polyacrylamide Gel Electrophoresis of Purified p10.

Figure 1:
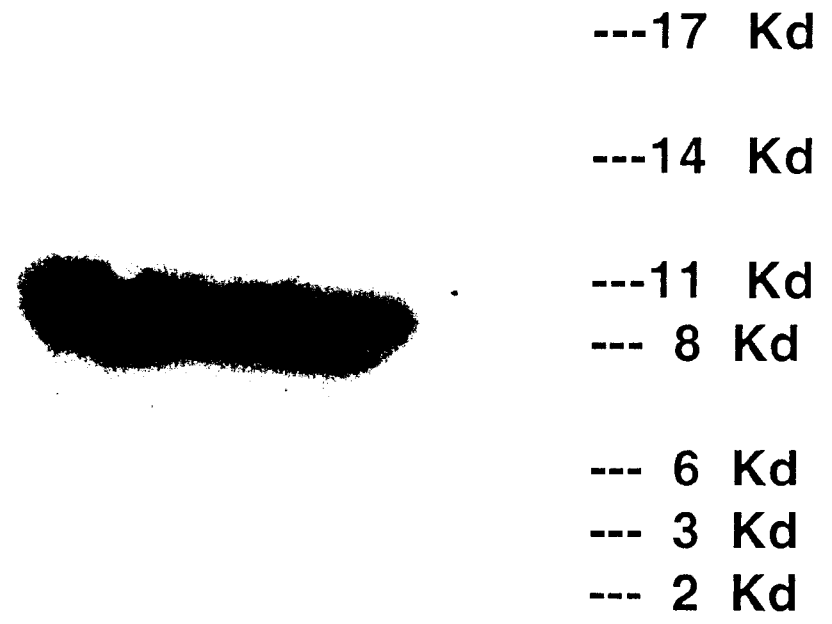

The cAMP eluant prepared as described in FIG. 1 was pooled and concentrated. The protein component that inhibited the GTP binding activity of H-Ras was further purified using the filter binding assay as described in FIG. 2. The purification procedure includes: DEAE high performance liquid chromatography, size exclusion chromatography and heat treatment. THe purified p10 was applied to a 15% polyacrylamide gel which was then developed and silver stained.

Figure 2:
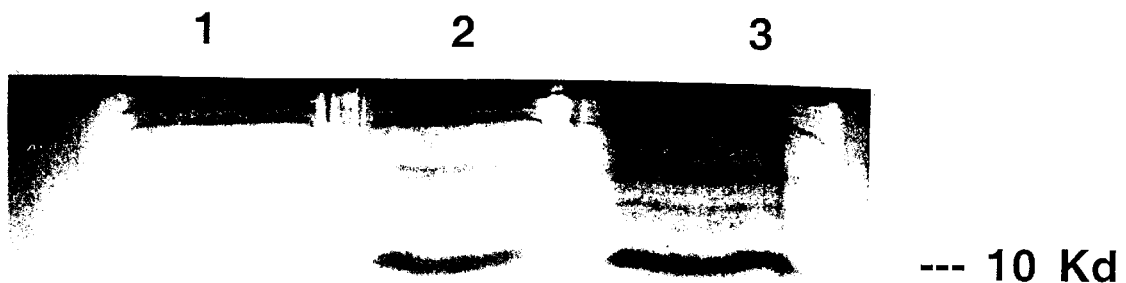

FIG. 2. Physical Association of p10 onto Immobilized Ras Affinity Resin.

The cAMP binding protein was isolated from a bovine brain cell extract by incubating 40 ml of bovine brain cell lysate (5 mg protein/ml) with 5 ml of cAMP agarose (Sigma) at 4° C. overnight. The cAMP agarose was then washed 5 times with 200 ml of Tris-HCl buffer (50 mM Tris, 50 mM NaCl, 5 mM $MgCl_2$, pH 7.5). The proteins that bound to the cAMP agarose were eluted with 5 ml of 10 mM cAMP dissolved in the same buffer. The cAMP eluant was then separated into high and low molecular weight fractions by passing the eluant through YM10 ultrafilter. The low molecular weight fraction (fraction passes through YM10 membrane, p10 fraction) was incubated with immobilized Ras Sepharose gel at 4° C. overnight, in the presence of 0.5 mg BSA. The immobilized Ras Sepharose gel was then washed with the same buffer to remove the unbound materials. The silica gel was then eluted with 10% SDS and the proteins were applied and separated on a 20% polyacrylamide gel and visualized by silver staining.

Figure 3:
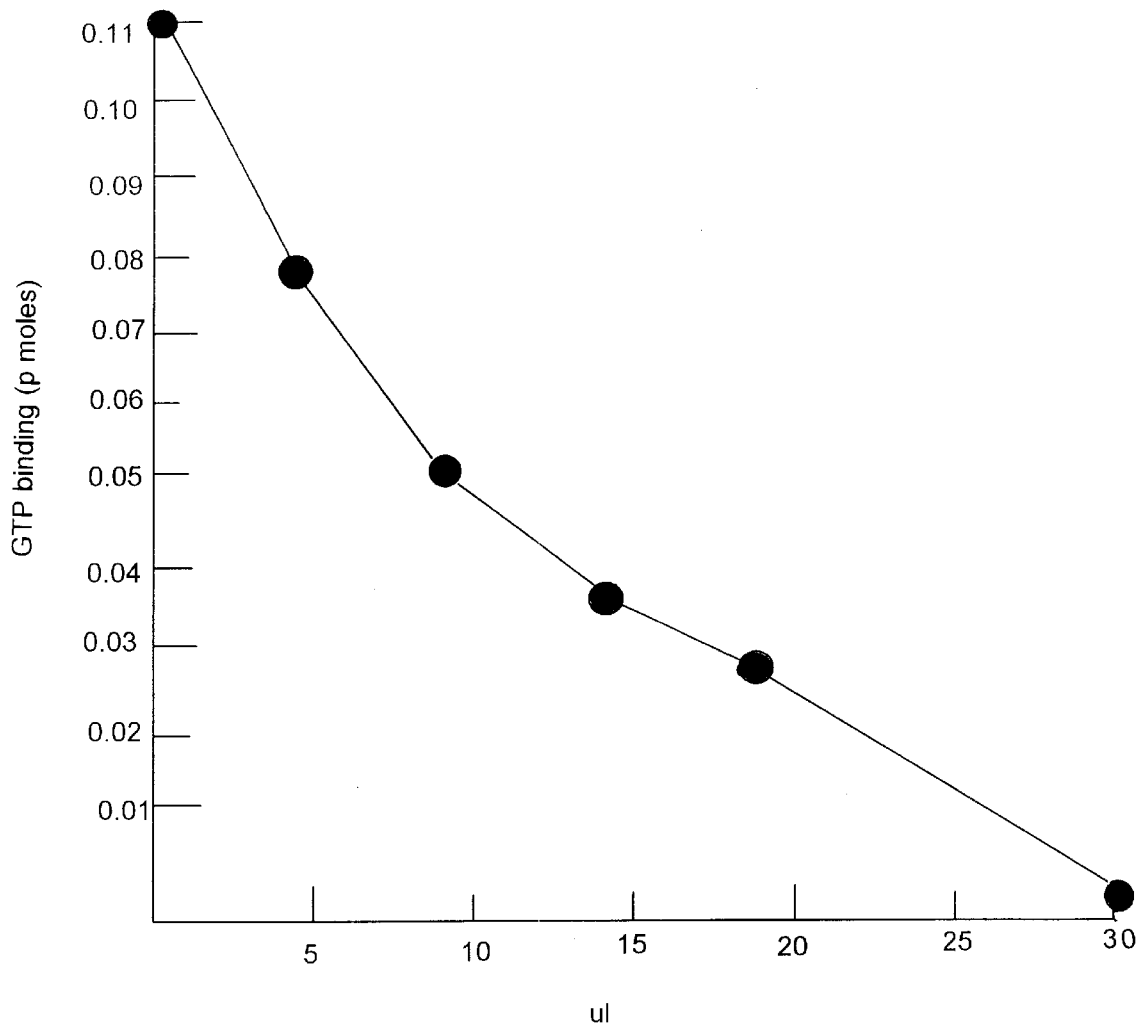

FIG. 3. Inhibition of H-Ras GTP Binding Activity by the p10 Fraction.

The P10 fraction was prepared as described in FIG. 1. The ability of various volumes of the p10 fraction to inhibit H-Ras GTP binding activity was examined by filter binding assay. Filter binding assay: Nucleotide-free H-Ras (0.25 pmoles) was incubated in 50 µl of Tris-HCl buffer (20 mM Tris-HCl, 5 mM $MgCl_2$, 0.1 M NaCl, 2 mM dithiothreitol, 0.5 mg/ml BSA, pH 7.5) with 0.66 pmoles alpha-P32 GTP (3000 Ci/mmol, NEN) in the presence or absence of the p10 fraction (containing 0.1 mM cAMP) at 30 degrees for 20 min. The reaction mixture was then applied to nitrocellulose filters (0.45 um, 25 mm; BA85, Schleicher & Schuell), which were immediately washed with 10 ml of 20 mM Tris-HCl (pH 7.5) containing 5 mM $MgCl_2$ and 50 mM NaCl. The amount of alpha-P-32 GTP remaining on the filter, which reflects the GTP binding activity of H-Ras, was then counted. In the absence of the p10 fraction, 0.11 pmoles of labeled GTP were bound to H-Ras, which accounts for 44% of the total Ras protein added.

Figure 4:
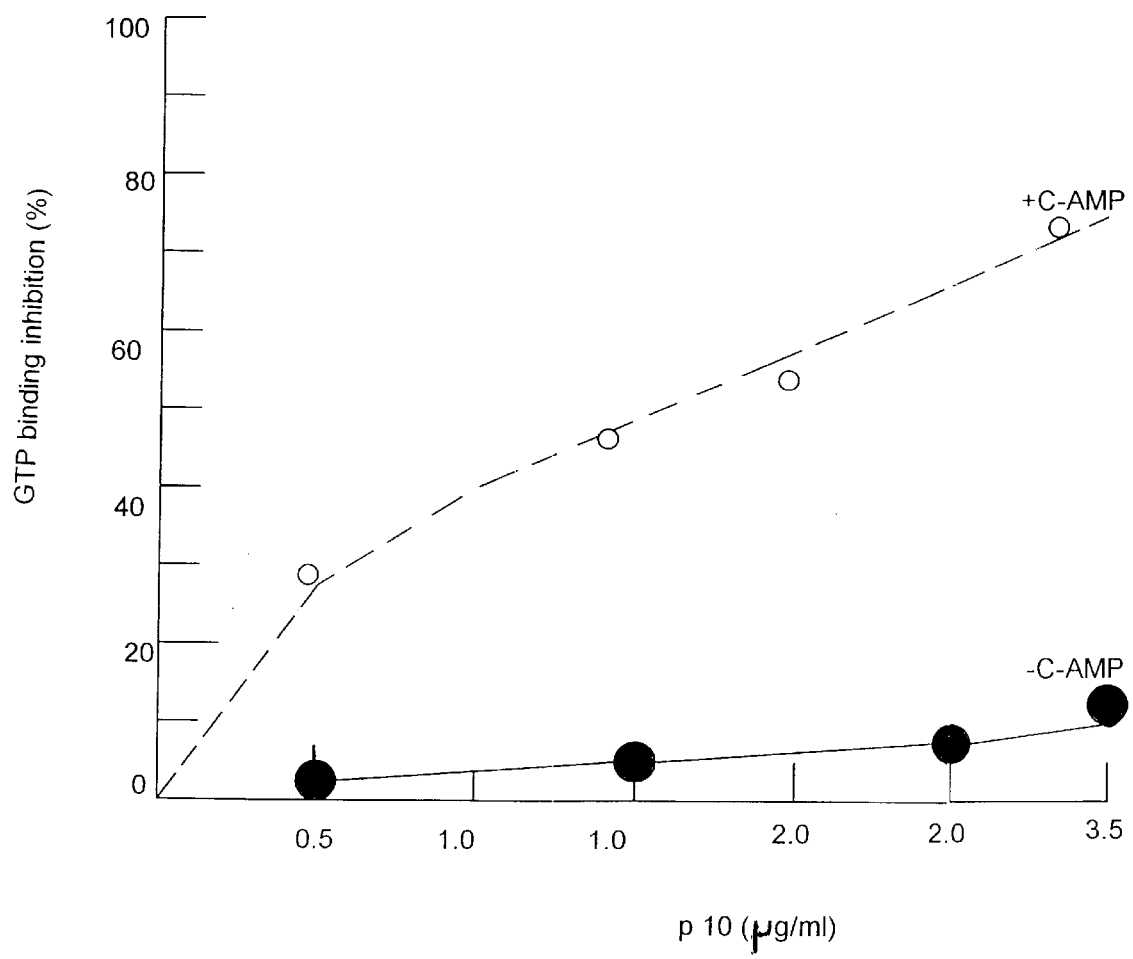

FIG. 4. Dose Response of the Inhibition of H-Ras GTP Binding Activity by the Purified p10 in the Presence or Absence of cAMP.

The small molecular weight cAMP binding protein (p10) which was purified as described in FIG. 2 was extensively dialyzed against 20 mM Tris-HCl (pH 7.5) for 2 days to remove bound cAMP. The GTP binding inhibitory activity was then examined by a filter binding assay and confirmed by a immunoprecipitation assay in the presence or absence of 0.1 mM cAMP. The Filter binding assay was performed as described in FIG. 2, except that 0.75 pmoles of H-Ras and 1.0 pmoles of alpha-P-32 GTP were used in this experiment. The Immunoprecipitiation assay was performed as follows: Bacterial synthesized H-Ras (0.75 pmoles) was incubated with alpha-P-32 GTP (1.0 pmoles) and various amounts of the purified protein in the presence or absence of 0.1 mM cAMP in 50 µl reaction buffer (20 mM Tris-HCl pH 7.5, 5 mM $MgCl_2$, 2 mM dithiothreitol, 0.1 M NaCl). After incubation at 30° C. for 20 min., Ras was immunoprecipitated by monoclonal antibody Y13-259 and protein A-Sepharose beads coated with rabbit antibody to immunoglobin G. The total alpha-P-32 GTP bound to Ras was then counted by a liquid scintillation counter: % inhibition=(Total count in the absence of protein−Total count in the presence of protein)/Total count in the absence of protein.

Figure 5:
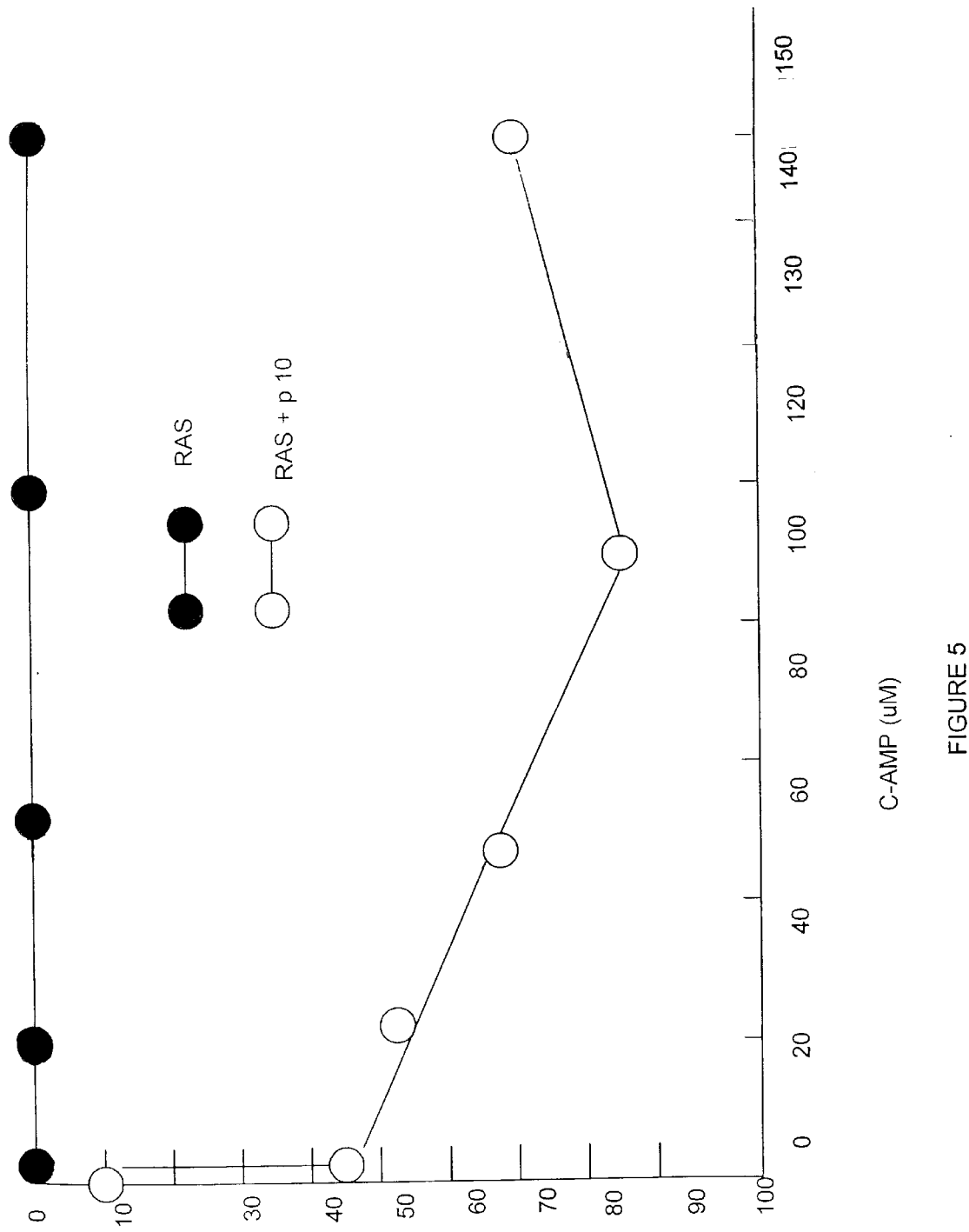

FIG. 5. cAMP Dependence of the Inhibition of H-Ras GTP Binding Activity by the Purified p10.

The highly purified p10 was dialyzed for 2 days, and the ability of this protein to inhibit the Ras GTP binding activity was then assayed at various cAMP concentrations as described in (A) using a filter binding assay cAMP alone did not affect the Ras GTP binding activity at any of the concentrations tested. The total count in the absence of the cAMP binding protein=12,170 CPM. % inhibition=(Total count in the absence of protein−Total count in the presence of protein/Total count in the absence of protein. Each point represents the average of duplicated results.

Figure 6:
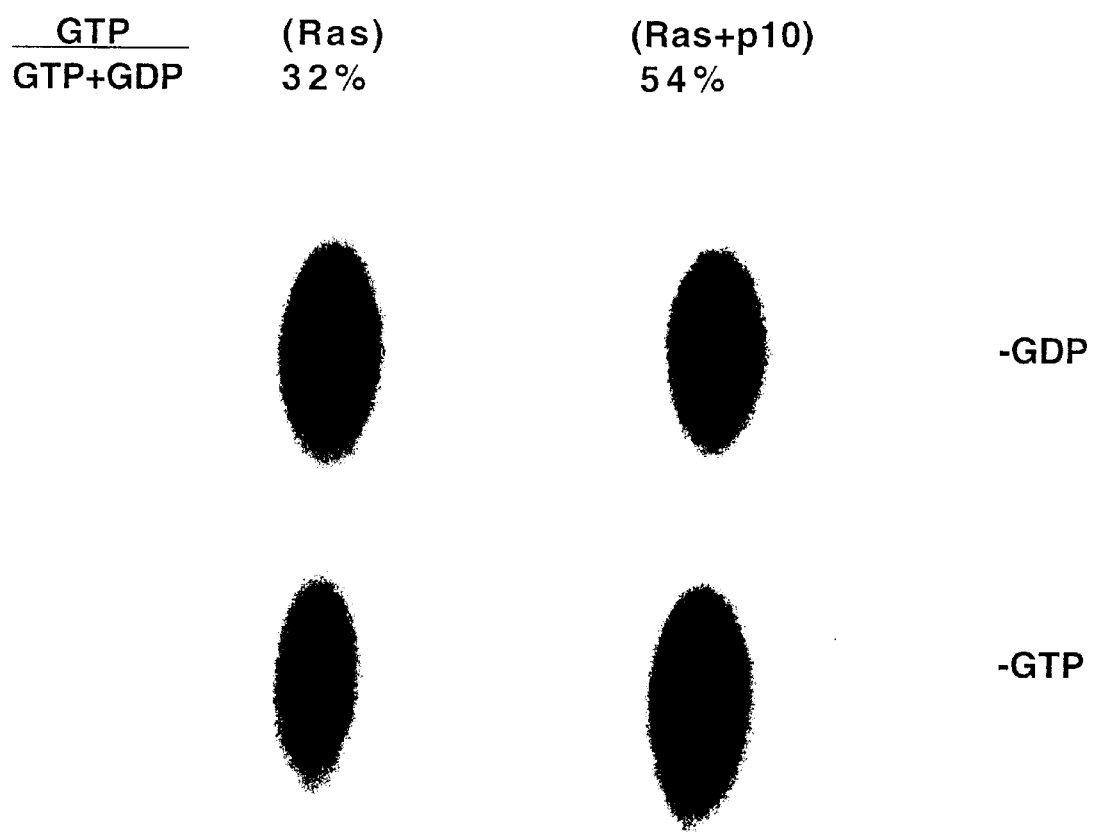

FIG. 6. p10 Inhibited Ras GTPase Activity in the Absence of cAMP

Dialyzed p10 (10 pmoles) prepared as described above was incubated with H-Ras (0.75 pmoles) in a Tris-HCl buffer (pH 7.5) containing 2 mM dithiothreitol, 1.0 pmole of alpha-p-32 GTP at 30 degrees for 20 minutes. The GTP hydrolysis activity of Ras was initiated by addition of 3 mM $MgCl_2$. After an incubation at 30 degrees for 30 minutes, Ras was immunoprecipitated by anti-Ras antibody Y13-259 and protein A-Sepharose coated with rabbit antibody to rat immunoglobulin G. Bound nucleotides were released from the immunoprecipitate by boiling for 3 minutes, resolved on polyethyleneimine cellulose thin layer chromatography plate (EM Science) in 1 mM potassium phosphate (pH. 3.4), visualized by autoradiography and quantitated by liquid scintillation counter.

Figure 7:
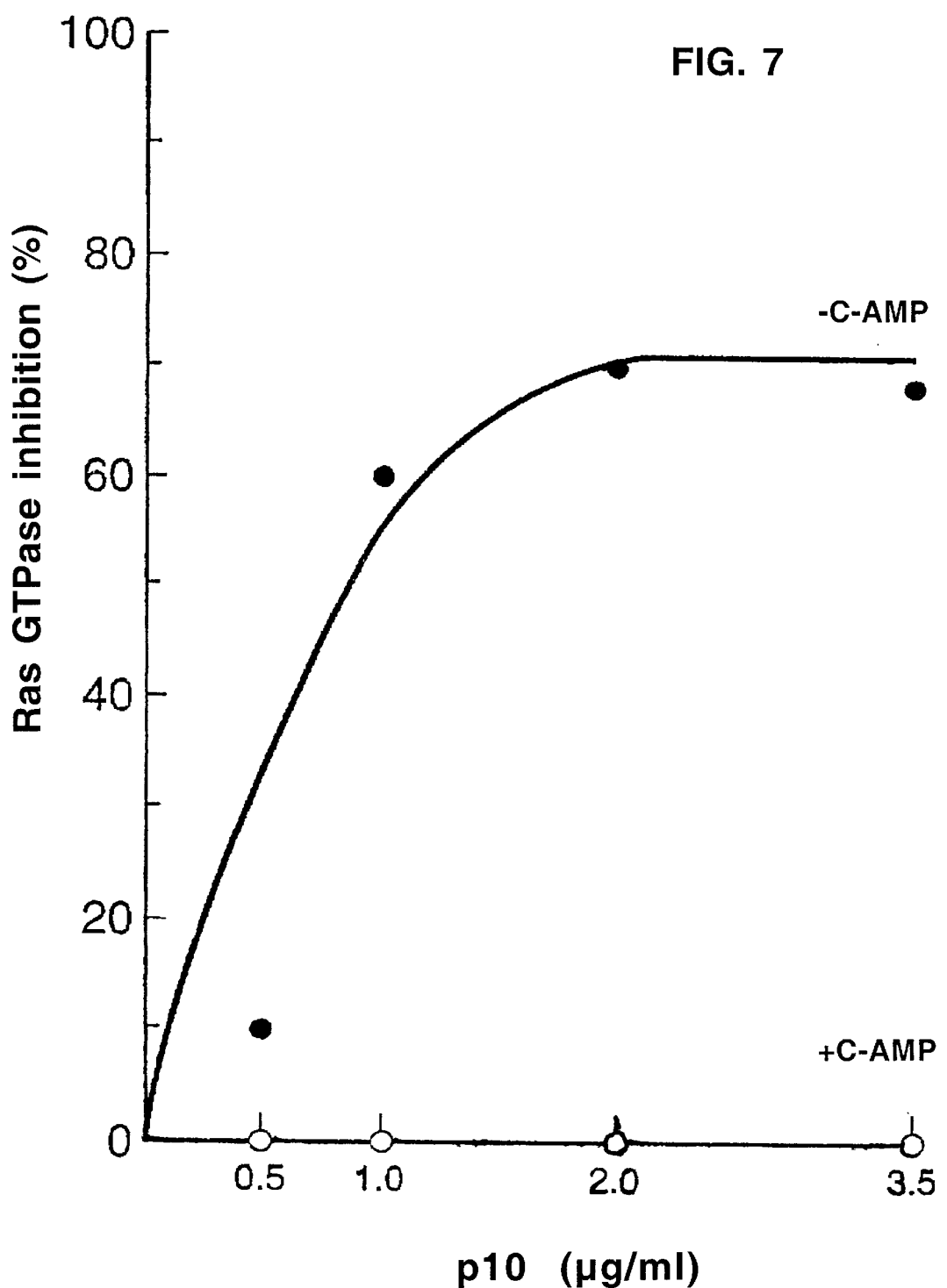

FIG. 7. Dose Dependence of the inhibitio of p10 on Ras GTPase Activity in the Absence of cAMP.

The GTPase activity of Ras in the preesnce of p10 was determined by the immunoprecipitation assay described in FIG. 6.

We claim:

1. A protein having a molecular weight of approximately 10 kD, wherein:

said protein is isolated and purified from clarified bovine brain cell lysate;
said protein binds specifically to Ras-GTP and Ras-GDP;
said protein does not bind to denatured Ras;
said protein inhibits GTP/GDP binding by Ras in the presence of cAMP;
said protein does not inhibit GTP/GDP binding by Ras in the absence of cAMP; and
said protein inhibits GTP hydrolysis by Ras in the absence of cAMP.

* * * * *